United States Patent [19]

Nilsson et al.

[11] Patent Number: 5,578,445
[45] Date of Patent: Nov. 26, 1996

[54] IN VITRO METHOD OF EVALUATING THE EFFECTS OF A SUBSTANCE

[75] Inventors: Stefan Nilsson, Ronninge; Mårten Osterlund, Stockholm; Karin Heeroma, Huddinge, all of Sweden

[73] Assignee: Karo Bio Aktiebolag, Huddinge, Sweden

[21] Appl. No.: 211,487

[22] PCT Filed: Oct. 6, 1992

[86] PCT No.: PCT/SE92/00698

§ 371 Date: Apr. 6, 1994

§ 102(e) Date: Apr. 6, 1994

[87] PCT Pub. No.: WO93/07290

PCT Pub. Date: Apr. 15, 1993

[30] Foreign Application Priority Data

Oct. 7, 1991 [SE] Sweden .................................. 9102901

[51] Int. Cl.$^6$ .......................... C12Q 1/68; G01N 33/567
[52] U.S. Cl. .................. 435/6; 435/7.1; 435/29; 436/500; 436/503
[58] Field of Search .................. 435/6, 7.1, 29; 436/500, 503

[56] References Cited

U.S. PATENT DOCUMENTS

| | | | |
|---|---|---|---|
| 4,859,585 | 8/1989 | Sonnenschein et al. | 435/29 |
| 5,266,464 | 11/1993 | Housey | 435/29 |
| 5,298,429 | 3/1994 | Evans et al. | 436/501 |

FOREIGN PATENT DOCUMENTS

| | | |
|---|---|---|
| WO91/07488 | 5/1991 | WIPO . |
| 9107488 | 5/1991 | WIPO . |

OTHER PUBLICATIONS

*Breast Cancer Research and Treatment*, vol. 17, 1990, Richard Poulin, et al.: "Multiple actions of synthetic progestins on the growth of ZR–75–1 human breast cancer cells: An in vitro model for the simultaneous assay of androgen, progestin, estrogen, and glucocorticoid agonistic and antagonistic activities of . . . ".

*Neuroendocrinology*, vol. 50, 1989, Steven M. Gabriel, et al., "Iso Stimulation of GH and cAMP: Comparison of beta–Adrenergic–to GRF–Stimulated GH Release and cAMP Accumulation in Monolayer Cultures of Anterior Pituitary Cells in vitro", pp. 170–176, see especially p. 171.

*Primary Examiner*—David Saunders
*Attorney, Agent, or Firm*—Banner & Allegretti, Ltd.

[57] ABSTRACT

An in vitro method of evaluating the antagonistic versus agonistic effects of a receptor-binding test substance on a selected type of cells containing endogenous intra-cellular hormone receptors, is disclosed. Said test substance, and separately a reference substance, known to be either an antagonist or an agonist, are incubated with said selected type of cells, and the magnitude of the selected cellular response resulting from hormone/receptor interaction, is analyzed. In case the method is performed on at least two selected types of cells which derive from different kinds of tissues, it is possible to evaluate the pattern of antagonistic versus agonistic effects of the selected test substance on said kinds of tissues.

14 Claims, No Drawings

IN VITRO METHOD OF EVALUATING THE EFFECTS OF A SUBSTANCE

The present invention relates to an in vitro method of evaluating the effects of a substance, especially the antagonistic versus agonistic effects of a receptor-binding substance, on a selected type of cells containing endogenous intra-cellular hormone receptors.

BACKGROUND

Efforts are made in the medical industry to reduce animal tests for the evaluation of the effects of substances which are candidates for incorporation into medicines. The reasons for this is i.a. the high costs and the comparatively long time needed for the experiments. Moreover, the extrapolation of the results from animal studies to humans does not always reflect the actual effects in humans.

There is an obvious need for screening methods which give species and tissue specific, comparatively reliable prediction of the effects of drug candidates.

In cases where the mechanism of action of drug candidates is known at the cellular level, it is possible to study the effects of the candidates in vitro. In such cases it should be possible to study the effects on cell lines derived from different types of tissues, and thus get a pattern of the effects in the studied types of tissues.

The present invention provides a tool for the prediction of the antagonistic versus agonistic effects of a receptor-binding substance on different kinds of tissues in a selected species.

DESCRIPTION OF THE INVENTION

The present invention is directed to an in vitro method of evaluating the antagonistic versus agonistic effects of a receptor-binding test substance on a selected type of cells containing endogenous intra-cellular hormone receptors. The method is carried out so a) that a sample of said cells, in a defined hormone-depleted first medium, is distributed into several separate culture containers, such as microtiter wells, b) that the containers of a) are incubated in a temperature and humidity controlled chamber for an appropriate time for the establishment of stable cell growth, c) that following b), the spent first medium is replaced by a defined hormone-depleted second medium, d) that the equally treated containers of b) are divided into four groups, $d_1$ to $d_4$, each comprising at least one container, $d^1$ to $d^4$, respectively, and each container being treated in the subsequent steps, e) that to the container:

$d^1$ is added said test substance, dissolved in a first solvent, at a known concentration, $d^2$ is added a reference substance, known to be either an antagonist or an agonist, dissolved in a second solvent, at a concentration known to result in a distinct cellular response selected to be analyzed, $d^3$ is added said first solvent and said second solvent, $d^4$ is added said test substance, dissolved in said first solvent, at the same concentration as used for $d^1$, and said reference substance, dissolved in said second solvent, at the same concentration as used for $d^2$, the first solvent and the second solvent being the same or different, and the amount of the first solvent and the amount of the second solvent not exceeding a level known to be harmful to the cells, f) that all the containers $d^1$ to $d^4$ are incubated in a temperature and humidity controlled chamber for a period of time sufficient for the substances to affect the cells to such a degree that a distinct cellular response selected to be analyzed is reached, g) that the incubated containers of f) are all analyzed with regard to the magnitude of the selected cellular response resulting from hormone/receptor interaction, and h) that the antagonistic versus agonistic effects of said test substance on said selected type of cells are evaluated from a comparison of the analyzed magnitudes of the selected cellular response obtained for said groups $d_1$ to $d_4$.

Thus, the method is directed to the evaluation of a test substance which is known to bind to intra-cellular hormone receptors. There are two possibilities, namely that the effects of the test substance are unknown or that the properties of the intra-cellular hormone receptors are unknown. The binding of the test substance to the intra-cellular hormone receptors of a selective type of cells may be confirmed by well-known methods in the art, e.g. binding studies.

The expression "cells containing endogenous intra-cellular hormone receptors" is intended to mean that intra-cellular hormone receptors are encoded by the unmanipulated genome of the cells, contrary to the case where the genes for the hormone receptors have been transfected into cells.

In one embodiment of the invention the first solvent and the second solvent used are both added to each of the containers $d^1$ to $d^4$, in the amounts used for the containers of the group $d_1$ and the group $d_2$, respectively. In this case the possible effect of different amounts of solvents in the containers are eliminated.

In another embodiment of the invention the cells of the selected type are anchorage dependent cells. Such cells have been used in the experimental part of this specification.

In yet another embodiment of the invention the containers $d^1$ of the group $d_1$ comprise increasing concentrations of said test substance. In this case it will be possible to simultaneously evaluate the effects of the test substance at different concentrations.

In still another embodiment of the invention the containers $d^2$ of the group $d_2$ comprise increasing concentrations of said reference substance. In this case it will be possible to evaluate the effects of the reference substance at different concentrations.

In an additional embodiment of the invention the containers $d^4$ of the group $d_4$ comprise increasing concentrations of said test substance, and comprise said reference substance at the same concentration as used for the containers $d^2$. In this case it will be possible to eliminate the possibility that the effect of the test substance is masked.

In yet another embodiment of the invention the cells of the selected type derive from mammalian bone, heart, breast or liver. In a preferred embodiment the cells of the selected type derive from human bone, heart, breast, liver or endometrium.

In a further embodiment of the invention the method is performed on at least two selected types of cells which derive from different kinds of tissues, thus enabling the evaluation of the pattern of antagonistic versus agonistic effects of the selected test substance on said kinds of tissues. In drug development it is of most importance to be able to evaluate the pattern of the antagonistic versus agonistic effects of a selected test substance on different kinds of tissues. In a preferred case of this embodiment the kinds of tissues derive from at least two members of the group consisting of mammalian and especially human bone, heart, breast, liver and endometrium.

In a preferred embodiment of the invention the cells of the selected type contain receptors which are members of the group consisting of steroid hormone receptors, thyroid hormone receptors and vitamin D receptors.

In a further embodiment, the steroid hormone receptors are selected from estrogen receptors and glucocorticoid receptors.

In still another embodiment of the invention the magnitude of the cellular response selected to be analyzed is the amount of a specific protein product, the gene expression of which is regulated by hormone/receptor interaction. The specific protein product is preferably an extra-cellular protein product, and is in one embodiment an endogenous protein product.

The selected cellular response resulting from hormone/receptor interaction need not be the expressed amount of a protein product, but may be e.g. the increase or decrease of the cell proliferation rate.

Further, the amount of an expressed protein product can be analyzed with the aid of an enzymatic assay or a commercial immunological assay using antibodies specifically directed to the selected protein product. Examples of conventional assays are ELISA (Enzyme Linked Immunosorbent Assay) and RIA (Radio Immunological Assay), but other assays are also known in the art.

Application of the invention on cells containing endogenous intra-cellular steroid and thyroid receptors.

Steroid and thyroid hormones have a common mechanism of action at the cellular level. Most of the unliganded receptors are nuclear proteins, except the glucocorticoid receptor which is considered to be cytoplasmic. The receptors can be divided into three domains: one domain binds to the hormone, one domain binds to DNA and the third domain seems to be important for interaction with other proteins. The mechanism of action is as follows: the hormone enters the cell either by passive diffusion or by other mechanisms and binds to the receptor. Upon binding of the ligand the receptor undergoes a conformational change, and becomes activated. This enables the receptor to bind to specific DNA sequences, so called hormone response elements which are located in the vicinity of hormonally regulated genes. The receptor interacts with transcription factors in order to regulate the expression of genes. There are certain transcription factors which are found in all cells and in addition there are transcription factors which are cell type specific. The regulation can be negative or positive depending on the promotor context and the collection of transcription factors found in the cell. What determines whether a hormonally regulated gene should be expressed in a cell is thus not only the presence of hormone and receptor but also cell specific transcription factor.

The present invention relies on cells having endogenous intra-cellular receptors, as opposed to the EP-A-0 287 653, where the genes for hormone receptors are transiently transfected into hormone receptor negative cells.

Thus, by testing hormone agonists and antagonists in a cell line derived from a tissue of interest for the specific indication it is possible to predict the effect in vivo at the cellular level.

Steroid and thyroid hormone analogs have been used in medicine for a long time. The use of these kinds of compounds frequently give rise to side effects because of their lack of tissue selectivity. There is a need for improved compounds with selective effect. Antiestrogens such as tamoxifen are used in the treatment of breast cancer. Many breast cancers are dependent on estrogens for growth and by blocking the receptor with antiestrogens, the tumor growth is inhibited. The use of tamoxifen is however associated with an incidence of new primary tumors at other sites such as the endometrium and the liver. This results from estrogenic activity of tamoxifen at these sites.

Hormone replacement therapy which means administration of estrogens to post menopausal women prevents osteoporosis. However, this therapy is not accepted in some countries because of the increased risk of breast cancer. A bone selective estrogen analogue would be a substantial improvement of osteoporosis therapy.

Examples of such genes which express gene products that can be measured to determine the antagonistic versus agonistic effects of a test compound in the method of the invention are listed below. These genes may be either positively or negatively regulated by hormones and this may occur only in certain celltypes.

Genes which are regulated by estrogens:
progesterone receptor
cathepsin D
TPA
pS2
urokinase
LDL receptor
alkaline phosphatase
IGF I
IGF II
TGF alpha
EGF receptor
jun (transcription factor)
fos (transcription factor)
myc Genes which are regulated by glucocorticoids:
tyrosine amine transferase (tat)
collagen
osteocalcin
NaKATPase
collagenase
urokinase Gene which is regulated by vitamin D3:
osteocalcin Genes which are regulated by thyroid hormones:
NaKATPase
beta-adrenergic receptors
growth hormone (Yaffe and Samuels, 1984, JBC 260, 6284–6291)
TSH (thyroid stimulating hormone) (Shupnik et al., 1985, JBC 260, 2900–2903)
malic enzyme (Towle et al., 1981, Biochemistry 20, 3486–3492) S14("spot14") (Liaw and Towle, 1984, JBC 259, 7253–7260) alpha myosin heavy chain (Izumo et al., 1984, Science 231, 591–600)
beta myosin heavy chain (Izumo et al., 1984, Science 231, 597–600)

Experiments performed making use of the method of the invention

Test and reference substances

Agonist: estradiol ($E_2$) (Sigma, product No E 1132)

Partial antagonist: tamoxifen (Tam) (a gift from Orion Corporation Farmos, Turku, Finland)

Antagonist: LY 117018 (a gift from Eli Lilly, USA; a non-steroidal benzothiophene, Endocrinology 113 (1983) 611–617)

Solvents:
0,01% - 0,5% in ethanol for estradiol 0,01% - 0,5% in ethanol for tamoxifen
0,01% - 0,5% in ethanol for LY 117018

Media:

First medium (A): Coon's medium without phenol red (manufactured by Statens Veterinärmedicinska Anstalt, Uppsala, Sweden, in accordance with instructions given in the SIGMA catalogue)
+10% fetal calf serum (FCS) [twice hormone-depleted with dextran coated charcoal (2×DCC)]
+1% non-essential amino acids (from Gibco-BRL)

Second medium (B): Coon's medium without phenol red
+1% FCS (2×DCC)
+5% serum substitute (purchased from Dr. Alan Preston, Med. Vet. supplies limited, Botolth Clayton, Buckingham, MK 18 2LR, U.K.)

First medium (C): Ham's F12 without phenol red (manufactured by Statens Veterinärmedicinska Anstalt, Uppsala, Sweden, in accordance with instructions given in the product catalogue of GIBCO-BRL)
+1% FCS (2×DCC)
+5% serum substitute (from Dr. Alan Preston)

pS2

Two experiments were conducted using the human breast cancer cell lines MCF7 (ATCC HTB 22) and ZR 75-1(ATCC CRL 1500) respectively. The selected cellular response to be analyzed was the amount of expressed protein pS2, the expression of which is regulated by the estrogene receptor. The agonist estradiol was Used as a reference substance and the effects of the partial antagonist tamoxifen was evaluated. The amount of pS2 secreted into the medium was determined with the aid of a commercial RIA (ELSA PS2 from CIS Bioindustries, Gif-sur-Yvette, France). The performance of the method is explained simultaneous for the two cell lines, for convenience.

Day 1:

Samples of the cells ZR75-1 ($8\times10^5$ cells) and MCF7 ($4\times10^5$ cells), respectively, were distributed into plastic petri-dishes (suitable for the culturing of mammalian cells). The cells were suspended in the first medium (A). Four dishes per cell line were used. These petridishes were incubated at 37° C. and 5% $CO_2$ in a temperature and humidity controlled chamber.

Day 5:

The first medium was replaced by the second medium. The following hormone additions were made:
one petridish/cell line—no hormone added
one petridish/cell line—+10 nM estradiol ($E_2$)
one petridish/cell line—+100 nM tamoxifen (Tam)
one petridish/cell line—+10 nM estradiol +100 nM tamoxifen The petridishes were incubated in the temperature and humidity controlled chamber under the same conditions as above.

Day 7:

48 hours after the hormone addition the number of cells and their morphology were investigated. Medium from each petridish was transferred to Eppendorf tubes and centrifuged 7 minutes at 1000rpm (Eppendorf centrifuge). The amount of pS2 in the medium samples was analyzed with the aid of a commercial pS2 RIA (ELSA PS2).

Results: The relative amount of pS2 secreted into the medium (the amount of pS2 secreted from the respective cell lines without added hormone is set at 1.)

|  | MCF7 | ZR-75-1 |
|---|---|---|
| no hormone added | 1 | 1 |
| +$E_2$(10 nM) | 1.39 | 3.73 |
| +Tam(100 nM) | 1.36 | 3.78 |
| +$E_2$(10 nM) + Tam(100 nM) | 0.74 | 1 |

It can be seen that the degree of induction of pS2 expression from the ZR-75-1 cells is higher than for the MCF7 cells, in the presence of $E_2$ alone (3.7× and 1.4×, respectively) or Tam alone (3.8× and 1.4×, respectively). The fact that tamoxifen can function as an agonist in human breast cancer cells, especially at low concentrations (<$10^{-6}$M) and in the absence of $E_2$ or phenol red in the culture medium, is previously known (see Br. J. Cancer (1989), 59: 727–738, and Cancer Res. (1988), 48: 3693–3697). This known fact is confirmed by the method of the invention. However, in the presence of both $E_2$ and Tam in the culture medium the expression of pS2 is inhibited to the same level (or lower) as in the absence of added hormone. This applies for both the ZR-75-1 and MCF7 cells.

It can be concluded that pS2 can be induced by $E_2$ in the breast cancer cell lines MCF7 and ZR-75-1. Further it can be concluded that $10^{-7}$M tamoxifen functions as agonist in both the cell lines MCF7 and ZR-75-1 in the absence of $E_2$. Furthermore, $10^{-7}$M tamoxifen functions as an antagonist in the presence of $10^{-8}$ M $E_2$.

Additional set of Experiments:

pS2

How the pS2 expression is regulated by estrogen in the human breast cancer cell lines MCF7 (ATCC HTB 22) and ZR 75-1 (ATCC CRL 1500), respectively, in the presence of the agonist estradiol, or the antagonists tamoxifen or LY 117019; or in the presence of both estradiol and tamoxifen, and estradiol and LY 117018, respectively, were tested. The amount of pS2 secreted into the medium was determined with the aid of a commercial RIA (ELSA pS2 from CIS Bioindustries, Gif-sur-Yvette, France).

Performance

Samples of the cells ZR 75-1 and MCF7, respectively, were distributed into plastic petridishes (suitable for the culturing of mammalian cells). The cells were suspended in the first medium (A) without 1% non-essential amino acids, but with 50 µg/ml gentamycin (from Gibco-BRL).

Day 5:

Samples of the cells ZR 75-1 ($4\times10^{-4}$ cells/well) and MCF7 ($2.5\times10^4$ cells/well), respectively, were distributed in 96-well trays. The cells were distributed in the same medium as used on day 1.

Day 6:

The wells were washed with 100 µl Coon's medium/well. The first medium was replaced by the second medium (B) without 1% FCS. The following hormone additions were made:

Experiment 1:

| 3 wells/hormone | No hormone added |
|---|---|
| " | +$10^{-11}$ M estradiol ($E_2$) |
| " | +$10^{-10}$ M $E_2$ |
| " | +$10^{-9}$ M $E_2$ |
| " | +$10^{-8}$ M $E_2$ |
| " | +$10^{-7}$ M $E_2$ |
| " | +$10^{-6}$ M $E_2$ |

Experiment 2:

| 3 wells/hormone | No hormone added |
|---|---|
| " | $+10^{-9}$ M Tamoxifen (Tam) |
| " | $+10^{-8}$ M Tam |
| " | $+10^{-7}$ M Tam |
| " | $+10^{-6}$ M Tam |
| " | $+10^{-10}$ M $E_2$ |
| " | $+10^{-10}$ M $E_2 + 10^{-9}$ M Tam |
| " | $+10^{-10}$ M $E_2 + 10^{-8}$ M Tam |
| " | $+10^{-10}$ M $E_2 + 10^{-7}$ M Tam |
| " | $+10^{-10}$ M $E_2 + 10^{-6}$ M Tam |

Experiment 3:

| 3 wells/hormone | No hormone added |
|---|---|
| " | $+10^{-9}$ M LY 117018 |
| " | $+10^{-8}$ M LY 117018 |
| " | $+10^{-7}$ M LY 117018 |
| " | $+10^{-6}$ M LY 117018 |
| " | $+10^{-10}$ M $E_2$ |
| " | $+10^{-10}$ M $E_2 + 10^{-9}$ M LY 117018 |
| " | $+10^{-10}$ M $E_2 + 10^{-8}$ M LY 117018 |
| " | $+10^{-10}$ M $E_2 + 10^{-7}$ M LY 117018 |
| " | $+10^{-10}$ M $E_2 + 10^{-6}$ M LY 117018 |

Day 8:

48 hours after the hormone addition the number of cells and their morphology were investigated. Medium from each well was transferred to Eppendorf tubes. The possible amount of pS2 in the medium samples was analyzed with the aid of a commercial pS2 RIA ( ELSA pS2 ).
Results:

Experiment 1: The relative amount of pS2 secreted into the medium in the presence of different concentration of $E_2$. The amount of pS2 secreted from their respective cell lines without added hormone is set at 1.

| | relative amount of pS2 | |
|---|---|---|
| | ZR 75-1 | MCF7 |
| No hormone added | 1 | 1 |
| $+10^{-11}$ M $E_2$ | 1.15 | 1.34 |
| $+10^{-10}$ M $E_2$ | 2.96 | 1.98 |
| $+10^{-9}$ M $E_2$ | 4.39 | 2.02 |
| $+10^{-8}$ M $E_2$ | 5.10 | 1.98 |
| $+10^{-7}$ M $E_2$ | 4.73 | 2.05 |
| $+10^{-6}$ M $E_2$ | 4.41 | 1.76 |

Experiment 2: The relative amount of pS2 secreted into the medium in the presence of different concentrations of Tam, and different concentrations of Tam in the presence of 0.1 nM $E_2$, respectively. The amount of pS2 secreted from the respective cell lines without added hormone is set at 1.

| | relative amount of pS2 | | | |
|---|---|---|---|---|
| | ZR 75-1 | | MCF7 | |
| | $-E_2$ | $+E_2$ | $-E_2$ | $+E_2$ |
| No Tam added | 1 | 9.24 | 1 | 1.91 |
| $+10^{-9}$ M Tam | 0.88 | 9.09 | 0.95 | 1.91 |
| $+10^{-8}$ M Tam | 0.98 | 9.39 | 0.97 | 1.89 |
| $+10^{-7}$ M Tam | 0.91 | 6.57 | 0.95 | 1.78 |
| $+10^{-6}$ M Tam | 0.94 | 1.28 | 0.94 | 1.18 |

Experiment 3: The relative amount of pS2 secreted into the medium in the presence of different concentrations of LY 117018, and different concentrations of LY 117018 in the presence of 0.1 nM $E_2$, respectively. The amount of pS2 secreted from the respective cell lines without added hormone is set at 1.

| | relative amount of pS2 | | | |
|---|---|---|---|---|
| | ZR 75-1 | | MCF7 | |
| | $-E_2$ | $+E_2$ | $-E_2$ | $+E_2$ |
| No LY 117018 added | 1 | 2.55 | 1 | 2.31 |
| $+10^{-9}$ M LY 117018 | 0.90 | 1.96 | 0.89 | 2.01 |
| $+10^{-8}$ M LY 117018 | 0.86 | 0.84 | 1.00 | 1.11 |
| $+10^{-7}$ M LY 117018 | 0.78 | 0.91 | 0.93 | 1.19 |
| $+10^{-6}$ M LY 117018 | 0.75 | 0.83 | 1.00 | 1.18 |

It can be seen that the degree of induction of pS2 expression from the ZR 75-1 cells and MCF7 cells is dependent on the concentration of $E_2$. An increased secretion of pS2 can be seen at 0.1 nM $E_2$. Maximal induction is reached at 1 nM. Tamoxifen and LY 117018, respectively, do not have an influence on the pS2 secretion. In the presence of both Tamoxifen and $E_2$ (0.1 nM) the expression of pS2 is inhibited at concentrations of Tam exceeding 100 nM. Maximal inhibition is seen at 1 µM Tamoxifen. LY 117018 functions as a stronger antagonist than Tamoxifen. In the presence of both 10 nM LY 117018 and 0.1 nM E2 in the culture medium the expression of pS2 is inhibited down to the same level as in the absence of added hormone in ZR 75-1 and also MCF7 cells.

It can be concluded that pS2 can be induced by $E_2$ in the breast cancer cell lines MCF7 and ZR 75-1. Maximal induction is seen at 1 nM $E_2$. Further, it can be concluded that $10^{-6}$M Tamoxifen functions as an antagonist in the presence of $10^{-10}$ M $E_2$. Furthermore, $10^{-8}$ M LY 117018 functions as an antagonist in the presence of $10^{-10}$ M $E_2$.

Cathepsin D

The experiment was conducted using the human breast cancer cell line MCF7 (ATCC HTB 22). The selected cellular response to be analyzed was the amount of expressed cathepsin D (Cath D), the expression of which is regulated by the estrogen receptor. The agonist estradiol was used as a reference substance and the effects of the partial antagonist tamoxifen or the antagonist LY 117018, respectively, were evaluated. Furthermore, the effects in the presence of both estradiol and tamoxifen, as well as the effects of both estradiol and LY 117018 were evaluated. The amount of Cath D secreted into the medium was determined with the aid of a commercial RIA (ELSA-CATH-D from CIS Bioindustries, Gif-sur-Yvette, France). The performance of the method is as follows:

Day 1:

A sample of the cell line MCF7 ($4\times10^5$ cells) was distributed into plastic petridishes (suitable for the culturing of mammalian cells). The cells were suspended in the first medium (C).

The petridishes were incubated at 37° C. and 5% $CO_2$ in a temperature and humidity controlled chamber.

Day 2:

The first medium (C) was replaced by the second medium, which consisted of fresh first medium (C). The following hormone additions were made:

| two petridishes/hormone addition | no hormone added |
|---|---|
| " | +10 nM estradiol ($E_2$) |
| " | +100 nM tamoxifen (Tam) |
| " | +100 nM LY 117018 |
| " | +10 nM estradiol + 100 nM tamoxifen |
| " | +10 nM estradiol + 100 nM LY 117018 |

The petridishes were incubated in the temperature and humidity controlled chamber under the same conditions as above.

Day 5:

72 hours after the hormone addition visual inspection of the number of cells and their morphology was performed. Medium from each petridish was transferred to Eppendorf tubes and centrifuged 7 minutes at 1000rpm (Eppendorf centrifuge). The amount of Cath D in the medium samples was analyzed with the aid of the commercial Cath D RIA (ELSA-CATH D)

Results: The relative amount of Cath D secreted into the medium (the amount of Cath D secreted from cells without added hormone is set at 1)

|   | relative amount of Cath D |
|---|---|
| 1. no hormone added | 1 |
| 2. +$E_2$ (10 nM) | 2.22 |
| 3. +Tam (100 nM) | 1.23 |
| 4. +LY 117018 (100 nM) | 0.88 |
| 5. +$E_2$ (10 nM) + Tam (100 nM) | 2.43 |
| 6. +$E_2$ (10 nM) + LY 117018 (100 nM) | 0.76 |

It can be seen that LY 117018 functions as an antagonist both in the absence and in the presence of $E_2$ (compare line 1, 4 and 6), whereas Tam shows weak agonism in the absence of $E_2$ (compare line 1 and 3) and no antagonism in the presence of $E_2$ (compare line 2 and 5). Tamoxifen is previously known to be a partial agonist in breast, especially at low concentrations ($<10^{-6}$M) and in the absence of $E_2$ or phenol red in the culture medium (as already stated in the experiment with pS2). The reason for Tam not to function as an antagonist in the presence of $E_2$ in this experiment as compared to the pS2 experiment may be due to the fact that the set up of the two experiments are not the same. A more interesting explanation may be that the mechanism underlying the ability of the estrogen receptor to regulate the expression of the genes Cath D and pS2, respectively, differs considerably, which may explain why 100 nM Tam (in the presence of 10 nM $E_2$) was enough for the down-regulation of pS2 but not Cath D (see Br.J. Cancer (1989), 59: 727–738).

It can be concluded that Cath D can be induced by $E_2$ in the breast cancer cell line MCF7, and that $10^{-7}$M tamoxifen functions as a weak agonist in the absence of $E_2$. Further, $10^{-7}$M tamoxifen does not function as an antagonist in the presence of $10^{-8}$M $E_2$. Finally $10^{-7}$M LY 117018 acts as an estrogen antagonist both in the absence and in the presence of $10^{-8}$M $E_2$.

Additional set of experiments:

Cathepsin D

How cathepsin D (Cath D) expression is regulated by estrogen in the human breast cancer cell lines MCF7 (ATCC HTB 22) and ZR 75-1 (ATCC CRL 1500), respectively, in the presence of the agonist estradiol, or the antagonists tamoxifen and LY 117018, respectively, or in the presence of both estradiol and tamoxifen, and estradiol and LY 117018, were tested. The amount of Cath D secreted into the medium was determined with the aid of a commercial RIA (ELSA-CATD-D from CIS Bio-industries, Gif-sur-Yvette, France).

Performance

Day 1:

Samples of the cells ZR 75-1 and MCF7, respectively, were distributed into plastic petridishes (suitable for the culturing of mammalian cells). The cells were suspended in the first medium (A) without 1% non-essential amino acids, but with 50 µg/ml gentamycin (from Gibco-BRL).

Day 5:

Samples of the cells ZR 75-1 ($4\times10^4$ cells/well) and MCF7 ($2.5\times10^4$ cells/well), respectively, were distributed in 96-well trays. The cells were distributed in the same medium as used on day 1.

Day 6:

The wells were washed with 100 µl Coon's medium/well. The first medium was replaced by the second medium (B) without 1% FCS. The following hormone additions were made:

Experiment 1:

| 3 wells/hormone | No hormone added |
|---|---|
| " | +$10^{-11}$ M estradiol ($E_2$) |
| " | +$10^{-10}$ M $E_2$ |
| " | +$10^{-9}$ M $E_2$ |
| " | +$10^{-8}$ M $E_2$ |
| " | +$10^{-7}$ M $E_2$ |
| " | +$10^{-6}$ M $E_2$ |

Experiment 2:

| 3 wells/hormone | No hormone added |
|---|---|
| " | +$10^{-9}$ M Tamoxifen (Tam) |
| " | +$10^{-8}$ M Tam |
| " | +$10^{-7}$ M Tam |
| " | +$10^{-6}$ M Tam |
| " | +$10^{-10}$ M $E_2$ |
| " | +$10^{-10}$ M $E_2$ + $10^{-9}$ M Tam |
| " | +$10^{-10}$ M $E_2$ + $10^{-8}$ M Tam |
| " | +$10^{-10}$ M $E_2$ + $10^{-7}$ M Tam |
| " | +$10^{-10}$ M $E_2$ + $10^{-6}$ M Tam |

Experiment 3:

| 3 wells/hormone | No hormone added |
|---|---|
| " | +$10^{-9}$ M LY 117018 |
| " | +$10^{-8}$ M LY 117018 |
| " | +$10^{-7}$ M LY 117018 |
| " | +$10^{-6}$ M LY 117018 |
| " | +$10^{-10}$ M $E_2$ |
| " | +$10^{-10}$ M $E_2$ + $10^{-9}$ M LY 117018 |
| " | +$10^{-10}$ M $E_2$ + $10^{-8}$ M LY 117018 |
| " | +$10^{-10}$ M $E_2$ + $10^{-7}$ M LY 117018 |
| " | +$10^{-10}$ M $E_2$ + $10^{-6}$ M LY 117018 |

Day 8:

48 hours after the hormone addition the number of cells and their morphology were investigated. Medium from each well was transferred to Eppendorf tubes. The possible amount of Cath D in the medium samples was analyzed with the aid of a commercial Cath D RIA (ELSA-CATH-D).

Results:

Experiment 1: The relative amount of Cath D secreted into the medium in the presence of different concentrations of $E_2$. The amount of Cath D secreted from the cells without added hormone is set at 1.

|  | relative amount of Cath D | |
|---|---|---|
|  | ZR 75-1 | MCF7 |
| No hormone added | 1 | 1 |
| +$10^{-11}$ M $E_2$ | 0.93 | 1.20 |
| +$10^{-10}$ M $E_2$ | 1.92 | 1.61 |
| +$10^{-9}$ M $E_2$ | 2.76 | 1.66 |
| +$10^{-8}$ M $E_2$ | 2.84 | 1.66 |
| +$10^{-7}$ M $E_2$ | 3.19 | 1.78 |
| +$10^{-6}$ M $E_2$ | 2.98 | 1.56 |

Experiment 2: The relative amount of Cath D secreted into the medium in the presence of different concentrations of Tam, and different concentrations of Tam in the presence of 0.1 nM $E_2$, respectively. The amount of Cath D secreted from the cells without added hormone is set at 1.

|  | relative amount of Cath D | | | |
|---|---|---|---|---|
|  | ZR 75-1 | | MCF7 | |
|  | $-E_2$ | $+E_2$ | $-E_2$ | $+E_2$ |
| No Tam added | 1 | 2.39 | 1 | 1.83 |
| + $10^{-9}$ M Tam | 1.06 | 2.16 | 0.99 | 1.78 |
| + $10^{-8}$ M Tam | 1.20 | 2.14 | 1.05 | 1.63 |
| + $10^{-7}$ M Tam | 0.88 | 2.07 | 0.97 | 1.58 |
| + $10^{-6}$ M Tam | 1.23 | 1.19 | 0.92 | 1.57 |

Experiment 3: The relative amount of Cath D secreted into the medium in the presence of different concentrations of LY 117018, and different concentrations of LY 117018 in the presence of 0.1 nM $E_2$, respectively. The amount of Cath D secreted from the cells without added hormone is set at 1.

|  | relative amount of Cath D | | | |
|---|---|---|---|---|
|  | ZR 75-1 | | MCF7 | |
|  | $-E_2$ | $+E_2$ | $-E_2$ | $+E_2$ |
| No LY 117018 added | 1 | 2.05 | 1 | 2.03 |
| + $10^{-9}$ M LY 117018 | 0.81 | 2.18 | 0.93 | 2.07 |
| + $10^{-8}$ M LY 117018 | 0.73 | 0.88 | 0.98 | 1.12 |
| + $10^{-7}$ M LY 117018 | 0.88 | 0.87 | 0.88 | 1.11 |
| + $10^{-6}$ M LY 117018 | 0.77 | 0.77 | 1.15 | 1.23 |

It can be seen that the degree of induction of Cath D in ZR 75-1 and MCF7 is dependent on the concentration of $E_2$. An increased secretion of Cath D can be seen at 0.1 nM $E_2$. Maximal induction is reached at 1 nM. Tamoxifen and LY 117018, respectively, do not have an influence on the Cath D secretion. In the presence of both Tamoxifen and $E_2$ (0.1 nM) the expression of Cath D is inhibited at concentrations of Tam of 1 μM in the ZR 75-1 cells. In MCF7 Tamoxifen functions as a weaker antagonist and at 1 μM a slight decrease in the amount of secreted Cath D can be seen. LY 117018 functions as a stronger antagonist than Tamoxifen. In the presence of both 10 nM LY 117018 and 0.1 nM $E_2$ in the culture medium the expression of Cath D is inhibited down to same level as in the absence of added hormone in the ZR 75-1 and also MCF7 cells.

It can be concluded that Cath D can be induced by $E_2$ in the breast cancer cell lines MCF7 and ZR 75-1. Maximal induction is seen at 1 nM $E_2$. Further, $10^{-6}$M Tamoxifen functions as an antagonist in the presence of $10^{-10}$M $E_2$ in the ZR 75-1 cells. Furthermore, $10^{-8}$M LY 117018 functions as an antagonist in the presence of $10^{-10}$M $E_2$.

Proliferation

How the human breast cancer cell lines MCF7 (ATCC HTB 22) and ZR 75-1 (ATCC CRL 1500), respectively, regulate their growth in the presence of the agonist estradiol, or the antagonists tamoxifen and LY 117018, and in the presence of both estradiol and tamoxifen, and estradiol and LY 117018, respectively, were tested. The growth is determined by measuring the amount of ATP in the cells after incubation with ligands for 6 days. The amount of ATP is determined with the aid of a method based on luciferin-luceferas reaction according to the manufacturer's instructions (LKB, Wallac).

Performance

Day 1:
Samples of the cells ZR 75-1 and MCF7, respectively, were distributed into plastic petridishes (suitable for the culturing of mammalian cells). The cells were suspended in the first medium (A) without 1% non-essential amino acids, but with 50 μg/ml gentamycin (from Gibco-BRL).

Day 2:
Samples of the cells ZR 75-1 (8000 cells/well) and MCF7 (4000 cells/well), respectively, were distributed into microtiter plates having 96 wells. The cells were suspended in the same medium as on day 1.

Day 6:
The first medium was replaced by a second medium (Ham's without phenol red +5% FCS (2×DCC)+50 μg/ml gentamycin +1% non-essential amino acids). The following hormone additions were made:

Experiment 1:

| 3 wells/hormone | No hormone added |
|---|---|
| " | + $10^{-9}$ Tamoxifen (Tam) |
| " | + $10^{-8}$ M Tam |
| " | + $10^{-7}$ M Tam |
| " | + $10^{-6}$ M Tam |
| " | + $10^{-10}$ M $E_2$ |
| " | + $10^{-10}$ M $E_2$ + $10^{-9}$ M Tam |
| " | + $10^{-10}$ M $E_2$ + $10^{-8}$ M Tam |
| " | + $10^{-10}$ M $E_2$ + $10^{-7}$ M Tam |
| " | + $10^{-10}$ M $E_2$ + $10^{-6}$ M Tam |

Experiment 2:

| 3 wells/hormone | No hormone added |
|---|---|
| " | + $10^{-9}$ M LY 117018 |
| " | + $10^{-8}$ M LY 117018 |
| " | + $10^{-7}$ M LY 117018 |
| " | + $10^{-6}$ M LY 117018 |
| " | + $10^{-10}$ M $E_2$ |
| " | + $10^{-10}$ M $E_2$ + $10^{-9}$ M LY 117018 |
| " | + $10^{-10}$ M $E_2$ + $10^{-8}$ M LY 117018 |
| " | + $10^{-10}$ M $E_2$ + $10^{-7}$ M LY 117018 |
| " | + $10^{-10}$ M $E_2$ + $10^{-6}$ M LY 117018 |

Day 9:
The medium was replaced by fresh medium of the same composition as on day 6, and hormone additions as on day 6.

Day 12:
6 days after hormone addition the number of cells and their morphology were investigated. Medium from each well was poured off. To each well was added 100 μl 1% TCA (trichloro acetic acid). After an incubation of 15 min the amount of ATP was measured according to a method based on the luciferin-luciferas reaction (LKB, Wallac).

Results:
Experiment 1: The relative amount of cells measured as the amount of ATP after culturing for 6 days in the presence of different concentrations of Tam, and different concentrations of Tam in the presence of 0.1 nM $E_2$, respectively. The amount of ATP without added hormone is set at 1.

|  | relative amount of ATP | | | |
|---|---|---|---|---|
|  | ZR 75-1 | | MCF7 | |
|  | $-E_2$ | $+E_2$ | $-E_2$ | $+E_2$ |
| No Tam added | 1 | 3.51 | 1 | 2.66 |
| + $10^{-9}$ M Tam | 0.91 | 3.57 | 0.96 | 3.41 |
| + $10^{-8}$ M Tam | 1.09 | 3.43 | 1.22 | 3.35 |
| + $10^{-7}$ M Tam | 1.55 | 3.55 | 1.09 | 2.28 |
| + $10^{-6}$ M Tam | 1.31 | 1.83 | 0.94 | 1.23 |

Experiment 2: The relative amount of cells measured as the amount of ATP after culturing for 6 days in the presence of different concentrations of LY 117018, and different concentrations of LY 117018, respectively, in the presence of 0.1 nM $E_2$. The amount of ATP without added hormone is set at 1.

|  | relative amount of ATP | | | |
|---|---|---|---|---|
|  | ZR 75-1 | | MCF7 | |
|  | $-E_2$ | $+E_2$ | $-E_2$ | $+E_2$ |
| No LY 117018 added | 1 | 4.68 | 1 | 2.30 |
| + $10^{-9}$ M LY 117018 | 1.03 | 3.07 | 0.85 | 1.17 |
| + $10^{-8}$ M LY 117018 | 0.89 | 0.91 | 0.89 | 0.93 |
| + $10^{-7}$ M LY 117018 | 0.99 | 1.03 | 0.89 | 0.78 |
| + $10^{-6}$ M LY 117018 | 0.69 | 0.63 | 0.27 | 0.55 |

It can be seen that the breast cancer cell lines ZR 75-1 and MCF7 increase their growth dramatically in the presence of 0.1 nM $E_2$. Tamoxifen has no effect on the growth of the MCF7 cells, but a weak agonistic effect of tamoxifen on ZR 75-1 can be seen at $10^{-7}$M. In the presence of both Tamoxifen and 0.1 nM $E_2$ the growth of MCF7 cells is inhibited at a Tamoxifen concentration exceeding $10^{-7}$M. Tamoxifen is a weaker antagonist in ZR 75-1, and not until at $10^{-6}$M Tamoxifen an antagonistic effect can be seen. LY 117018 functions as a stronger antagonist than Tamoxifen. In the presence of both 0.1 nM $E_2$ and 10 nM LY 117018 in the culture medium the growth of both the cells MCF7 and ZR 75-1 are inhibited down to the same level as in the absence of added hormone.

It can be concluded that 0.1 nM $E_2$ stimulates the growth of the breast cancer cell lines MCF7 and ZR 75-1. Further, $10^{-7}$M Tamoxifen functions as an antagonist in the presence of $10^{-10}$M $E_2$ in the MCF7 cells. Also, $10^{-7}$M Tamoxifen functions as a weak agonist in ZR 75-1 cells. Furthermore, $10^{-7}$M LY 117018 functions as an antagonist in the presence of $10^{-10}$M $E_2$ in MCF7 and ZR 75-1 cells.

Alkaline phosphatase

The experiment was conducted using a reporter cell line (ZR 75-AF) which had been constructed by a stable transfection of the human breast cancer cell line ZR 75-1 (ATCC CRL 1500) with a plasmid comprising estrogen responsive element (ERE) and alkaline phosphatase (Alk. phos.) as reporter protein. The selected cellular response to be analyzed was thus the amount of expressed Alk. phos., the expression of which is regulated by the estrogen receptor. The expression of Alk. phos. is studied in the presence of various concentrations of the agonist estradiol, the antagonist tamoxifen and in the presence of both estradiol and tamoxifen. The amount of Alk. phos. secreted into the medium was determined by a chemiluminiscence method based on AMPPD (disodium 3-[4-methoxyspiro[1,2-dioxithane-3,2'-tricyclo[3.3.1]decan]-4-yl]Phenyl phosphate) (Tropix Inc, USA) as substrate.

The method is conducted in the following way:

Day 1:
A sample of the cells ZR 75-AF was distributed into plastic petridishes (suitable for the culturing of mammalian cells). The cells were suspended in the first medium (A). These petridishes were incubated at 37° C. and 5% $CO_2$ in a temperature and humidity controlled chamber.

Day 4:
A sample of the cells ZR 75-AF ($4 \times 10^4$ cells/well) was distributed into a micro titer plate having 96 wells. The cells were suspended in fresh first medium (A). The plate was incubated at 37° C. and 5% $CO_2$ in a temperature and humidity controlled chamber.

Day 6:
The first medium (A) was replaced by the second medium (B).

The following hormone additions were made:
Experiment 1:

| 3 wells/hormone | no hormone added |
|---|---|
| " | + $10^{-12}$ M estradiol ($E_2$) |
| " | + $10^{-11}$ M $E_2$ |
| " | + $10^{-10}$ M $E_2$ |
| " | + $10^{-9}$ M $E_2$ |
| " | + $10^{-8}$ M $E_2$ |
| " | + $10^{-7}$ M $E_2$ |

Experiment 2:

| 3 wells/hormone | no hormone added |
|---|---|
| " | + $10^{-10}$ M Tamoxifen (Tam) |
| " | + $10^{-9}$ M Tam |
| " | + $10^{-8}$ M Tam |
| " | + $10^{-7}$ M Tam |
| " | + $10^{-6}$ M Tam |
| " | + $5 \times 10^{-6}$ M Tam |
| " | + 1 nM $E_2$ |
| " | + 1 nM $E_2$ + $10^{-10}$ M Tam |
| " | + 1 nM $E_2$ + $10^{-9}$ M Tam |
| " | + 1 nM $E_2$ + $10^{-8}$ M Tam |
| " | + 1 nM $E_2$ + $10^{-7}$ M Tam |
| " | + 1 nM $E_2$ + $10^{-6}$ M Tam |
| " | + 1 nM $E_2$ + $5 \times 10^{-6}$ M Tam |

Day 8:
48 hours after the hormone addition the number of cells and their morphology were investigated. Medium from each well was transferred to Eppendorf tubes and incubated at 65° C. for 10 minutes. The relative amount of Alk. phos. was then determined by a chemiluminiscence assay (Tropix Inc., USA).

Results:
Experiment 1: The relative amount of Alk. phos. secreted into the medium in the presence of various concentrations of $E_2$ (the amount of Alk. phos. secreted without hormone addition is set at 1).

|  | relative amount of Alk. phos. |
|---|---|
| no hormone added | 1 |
| + $10^{-12}$ M $E_2$ | 1.05 |
| + $10^{-11}$ M $E_2$ | 1.12 |
| + $10^{-10}$ M $E_2$ | 3.26 |
| + $10^{-9}$ M $E_2$ | 5.67 |
| + $10^{-8}$ M $E_2$ | 6.85 |
| + $10^{-7}$ M $E_2$ | 7.90 |

Experiment 2: The relative amount of Alk. phos. secreted into the medium in the presence of various concentrations of Tam and various concentrations of Tam in the presence of 1 nM $E_2$ (the amount of Alk. phos. secreted without hormone addition is set at 1)

|  | relative amount of Alk. phos. | |
|---|---|---|
|  | $-E_2$ | +1 nM $E_2$ |
| no Tam added | 1 | 8.97 |
| + $10^{-10}$ M Tam | 1.13 | 9.50 |
| + $10^{-9}$ M Tam | 1.08 | 9.12 |
| + $10^{-8}$ M Tam | 1.27 | 10.28 |
| + $10^{-7}$ M Tam | 1.80 | 7.57 |
| + $10^{-6}$ M Tam | 3.11 | 3.65 |
| + $5 \times 10^{-6}$ M Tam | 2.87 | 2.62 |

It can be seen that the degree of induction of heat stable Alk. phos. from the reporter cell line ZR 75-AF is dependent on the concentration of $E_2$. An increased secretion of Alk. phos.

can be seen at already $10^{-10}$M $E_2$. At $10^{-7}$M $E_2$ the degree of induction of 7.9 is reached. Tamoxifen ($10^{-7}$M) alone functions as a weak agonist. A maximum agonistic effect is reached at $10^{-6}$M Tamoxifen. As is earlier stated herein, it is previously known that Tamoxifen may function as an agonist in human breast cancer cells in the absence of $E_2$ or phenol red in the culture medium. In the presence of both Tamoxifen and $E_2$ (1 nM) the expression of Alk. phos. is inhibited by Tamoxifen concentrations exceeding $10^{-7}$M. Maximum inhibition is reach at $10^{-6}$M Tamoxifen.

It can be concluded that Alk. phos. can be induced by $E_2$ in the reporter cell line ZR 75-A37. Further, it can be concluded that Tamoxifen in a concentration of $10^{-6}$M functions as an agonist in the absence of $E_2$. Moreover, Tamoxifen at a concentration of $10^{-6}$M functions as an antagonist in the presence of $10^{-9}$M $E_2$.

In order to study the effects of ligands to the thyroid hormone receptor in liver, the following experiment was conducted:

The effect of T3 on the expression of steroid hormone binding globulin (SHBG), in human liver cells.

In this experiment we analyze the effect of the hormone 3,3',5-Triiodothyronine (T3) (agonist: purchased from Sigma, cat. no. T 6397) on the expression of sex (steroid) hormone binding globulin (SHBG) in the human liver cell line HepG2 (ATCC HB 8065). The level of SHBG, secreted into the culture medium is determined by a commercially available SHBG Delfia assay (manufactured by Wallac OY, Turku, Finland).

Two different variants of HepG2 were used in this study designated HepG2:1 and HepG2:2.

Experimental design
Day 1:

Approximately $1\times 10^6$ cells were seeded in 6-well plastic petri-dishes (suitable for growth of mammalian cells) in 2 ml of the first medium (A). Six wells per cell line were used. These culture plates were incubated at 37° C. and 5% $CO_2$ in a temperature and humidity controlled cell incubator.

Day 2:

The first medium was aspirated and the cells were rinsed once with Coon's (without any additions) and then refed with 1 ml of the second medium (B) [without 1% FCS (2×DCC)]. The following hormone additions were made:

| two wells/cell line | no hormone added |
| " | + $10^{-8}$ M T3 |
| " | + $10^{-7}$ M T3 |

The culture plates were incubated in the temperature and humidity controlled cell incubator under the same conditions as above.

Day 4:

48 hours after the addition of hormone the condition of the cells and their morphology were examined by visual inspection in the microscope. Medium from each well was transferred to Eppendorf tubes and centrifuged at 1000 rpm for seven minutes in an Eppendorf centrifuge. The supernatants were transferred to fresh Eppendorf tubes and the amount of SHBG in 25 μl of the conditioned medium was determined by an SHBG Delfia assay (Wallac Oy, Turku, Finland) according to the manufacturer's instructions.

Results:

The relative amount of SHBG expressed and secreted by the HepG2 cell lines in the presence or absence of T3 (the level of SHBG secreted from the cells in the absence of added hormone is set at 1)

| | HepG2:1 | HepG2:2 |
|---|---|---|
| no hormone added | 1 | 1 |
| + $10^{-8}$ M T3 | 1.6 | 16 |
| + $10^{-7}$ M T3 | 1.6 | 18 |

As shown in the table the inducibility of SHBG is greater in the HepG2:2 variant. The reason for the discrepancy in T3 inducibility of the SHBG expression in HepG2:1 cells compared to HepG2:2 cells is not known. However, it is a well known fact that the behaviour of different versions of originally one and the same cell line can differ depending on the conditions under which they have been cultivated. Whether HepG2:2 represents an isolated clone from the original population of HepG2 cells is not known.

It can be concluded from the experiment that T3 can induce the expression of SHBG in both HepG2:1 and HepG2:2.

We claim:

1. An in vitro method of evaluating the pattern of antagonistic versus agonistic effects of a receptor-binding test substance on at least two selected types of cells which contain endogenous intra-cellular hormone receptors and which derive from different kinds of tissues, characterized in that steps a)–h) are performed separately for each selected type of cells:
   a) that a sample of said cells, in a defined hormone-depleted first medium, is distributed into several separate culture containers,
   b) that the containers of step a) are incubated in a temperature and humidity controlled chamber for an appropriate time to establish stable cell growth,
   c) that following step b), spent first medium in the containers is replaced by a defined hormone-depleted second medium,
   d) that the containers of step e) are divided into four groups, $d_1$ to $d_4$, each comprising at least one container, $d^1$ to $d^4$, respectively, and each container being treated in subsequent steps,
   e) that to the container:
      $d^1$ is added said test substance, dissolved in a first solvent, at a known concentration,
      $d^2$ is added a reference substance, known to be either an antagonist or an agonist, dissolved in a second solvent, at a concentration known to result in a distinct cellular response selected to be analyzed,
      $d^3$ is added said first solvent and said second solvent,
      $d^4$ is added said test substance, dissolved in said first solvent, at the same concentration as used for $d^1$, and said reference substance, dissolved in said second solvent, at the same concentration as used for $d^2$,
      the first solvent and the second solvent being the same or different, and the amount of the first solvent and the amount of the second solvent not exceeding a level known to be harmful to the cells,
   f) that all the containers $d^1$ to $d^4$ are incubated in a temperature and humidity controlled chamber for a period of time sufficient for the substances to affect the cells to such a degree that a distinct cellular response selected to be analyzed is reached,
   g) that the incubated containers of step f) are all analyzed with regard to the magnitude of the selected cellular response resulting from hormone/receptor interaction, and
   h) that the antagonistic versus agonistic effects of said test substance on said selected type of cells are evaluated from a comparison of the analyzed magnitudes of the selected cellular response obtained for said groups $d_1$ and $d_4$, and the results obtained for each selected type of cells form together the pattern of antagonistic versus agonistic effects of said receptor-binding test substance on said selected different kinds of tissues.

2. A method according to claim 1, wherein said first solvent and said second solvent are both added to each of the containers $d^1$ to $d^4$, in the amounts used for the containers of the group $d_1$ and the group $d_2$, respectively.

3. A method according to claim 1, wherein the cells of the selected types are anchorage dependent cells.

4. A method according to claim 1, wherein the containers $d^1$ of the group $d_1$ comprise increasing concentrations of said test substance.

5. A method according to claim 1, wherein the containers $d^2$ of the group $d_2$ comprise increasing concentrations of said reference substance.

6. A method according to claim 1, wherein the containers $d^4$ of the group $d_4$ comprise increasing concentrations of said test substance, and comprise said reference substance at the same concentration as used for the containers $d^2$.

7. A method according to claim 1, wherein the cells of the selected types derive from mammalian bone, heart, breast, liver or endometrium.

8. A method according to claim 7, wherein the cells of the selected types derive from human bone, heart, breast, liver or endometrium.

9. A method according to claim 1, wherein the cells of the selected types contain receptors selected from the group consisting of steroid hormone receptors, thyroid hormone receptors and vitamin D receptors.

10. A method according to claim 9, wherein the steroid hormone receptors are selected from the group consisting of estrogen receptors and glucocorticoid receptors.

11. A method according to claim 1, wherein the magnitude of the cellular response selected to be analyzed is the amount of a specific protein product, gene expression of which is regulated by hormone/receptor interaction.

12. A method according to claim 11, wherein the specific protein product is an extracellular protein product.

13. A method according to claim 11 or 12, wherein the specific protein product is an endogenous protein product.

14. The method of claim 1 wherein the culture containers are microtiter wells.

* * * * *

UNITED STATES PATENT AND TRADEMARK OFFICE
CERTIFICATE OF CORRECTION

PATENT NO.   : 5,578,445
DATED        : November 26, 1996
INVENTOR(S)  : Stefan Nilsson, et. al.

It is certified that error appears in the above-indentified patent and that said Letters Patent is hereby corrected as shown below:

Title page, under OTHER PUBLICATIONS, change "progestins" to -- 'progestins'--.

Column 16, line 36, (claims) change "step e)" to --step c)--.

Signed and Sealed this

Third Day of June, 1997

Attest:

BRUCE LEHMAN

Attesting Officer       Commissioner of Patents and Trademarks